(12) United States Patent
Link

(10) Patent No.: US 9,744,045 B2
(45) Date of Patent: Aug. 29, 2017

(54) ENDOPROSTHESIS FOR THE PARTIAL REPLACEMENT OF THE HUMAN PELVIC BONE

(71) Applicant: Waldemar Link GmbH & Co. KG, Hamburg (DE)

(72) Inventor: Helmut D Link, Hamburg (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 0 days.

(21) Appl. No.: 14/763,728

(22) PCT Filed: Jan. 16, 2014

(86) PCT No.: PCT/EP2014/050798
§ 371 (c)(1),
(2) Date: Jul. 27, 2015

(87) PCT Pub. No.: WO2014/121994
PCT Pub. Date: Aug. 14, 2014

(65) Prior Publication Data
US 2015/0351917 A1   Dec. 10, 2015

(30) Foreign Application Priority Data
Feb. 8, 2013 (EP) ..................................... 13154638

(51) Int. Cl.
*A61F 2/34* (2006.01)
*A61F 2/32* (2006.01)
(Continued)

(52) U.S. Cl.
CPC ............ *A61F 2/32* (2013.01); *A61F 2/30734* (2013.01); *A61B 17/8066* (2013.01); *A61F 2/34* (2013.01);
(Continued)

(58) Field of Classification Search
CPC ............... A61F 2/34; A61F 2002/3406; A61F 2002/3429; A61F 2/32
See application file for complete search history.

(56) References Cited

U.S. PATENT DOCUMENTS 6,004,353 A * 12/1999 Masini ............... A61B 17/8066
623/22.21
2003/0171818 A1   9/2003 Lewallen
(Continued)

FOREIGN PATENT DOCUMENTS

CN   102048598   5/2011
DE   19700160   8/1998
(Continued)

*Primary Examiner* — Jason-Dennis Stewart
(74) *Attorney, Agent, or Firm* — Sand & Sebolt

(57) ABSTRACT

An endoprosthesis for partial replacement of the human pelvic bone (B) in the region of the acetabulum and of the ilium (II), by means of which a single prosthesis provides a bone replacement and stabilization in the region of the acetabulum and in defective sections of the ilium (II). The endoprosthesis, is suitable for restoring one single piece, even for serious bone defects in the pelvic region, and for maintaining or reshaping articulation and mobility in this region. The endoprosthesis includes a first section having a first partially spherical recess that serves as a replacement for the acetabulum, and a second section for the contact elements on the ilium (II). The second section extends from the first section along an edge of the first partially spherical recess in a flattened manner and is integrally connected to the first section. A second partially spherical recess is provided in the second section.

14 Claims, 3 Drawing Sheets

(51) Int. Cl.
*A61F 2/30* (2006.01)
*A61B 17/80* (2006.01)
(52) U.S. Cl.
CPC ............... *A61F 2002/3079* (2013.01); *A61F 2002/30245* (2013.01); *A61F 2002/30576* (2013.01); *A61F 2002/30736* (2013.01); *A61F 2002/30772* (2013.01); *A61F 2002/30784* (2013.01)

(56) References Cited

U.S. PATENT DOCUMENTS

| | | | |
|---|---|---|---|
| 2003/0212459 | A1 | 11/2003 | Gibbs |
| 2006/0116775 | A1 | 6/2006 | White |
| 2012/0109331 | A1* | 5/2012 | Meridew ............ A61F 2/30756 623/22.21 |

FOREIGN PATENT DOCUMENTS

| | | |
|---|---|---|
| DE | 19747357 | 7/1999 |
| DE | 69729265 | 6/2005 |
| WO | 88/01491 | 3/1988 |

* cited by examiner

ENDOPROSTHESIS FOR THE PARTIAL REPLACEMENT OF THE HUMAN PELVIC BONE

TECHNICAL FIELD

The present invention relates to an endoprosthesis for the partial replacement of the human pelvic bone in the region of the acetabulum as well as the os ilium (iliac bone) with the features of a first section which has a first partially spherical recess that serves as a replacement for the acetabulum, as well as a second section for resting against the os ilium (II), characterized in that the second section proceeding from the first section extends flattened beyond the edge of the first partially spherical recess and is integrally connected to the first section, and a second partially spherical recess is introduced in the second section.

BACKGROUND OF THE INVENTION

It is known that the natural bone structure is affected and can change from wear, bone weakness (such as osteoporosis) or other osseous changes caused by disease such as tumor diseases in the pelvic area so that the bone statics fail, and/or the joint function, especially that of the acetabulum. Corresponding damage and failure at this location can also occur as a result of accidents and complicated fractures.

Frequently, these are instances in which only the pelvic-side part of the hip joint, the acetabulum and its directly adjacent areas, is affected. In these cases, hip endoprostheses are inserted; an artificial socket component is inserted and anchored in the pelvic bone in a patient's existing pelvis which is otherwise intact in regard to its bone structure and load-bearing capacity instead of the defective, natural acetabulum.

In such cases, however, in which large parts of the pelvic bone are defective and affected, more extensive replacements are necessary.

CN 102048598 A discloses a partial pelvic replacement in which the entire os ilium is replaced in addition to the acetabulum formed thereupon as well as at least part of the os ischium, or the entire os ischium in one version of the embodiment, when there is particularly massive damage to the natural pelvic bone.

The endoprosthesis of the invention is for less extensive and serious replacements, however, and relates to endoprostheses for the partial replacement of the human pelvic bone which cover the region of the acetabulum as well as part of the os ilium.

Comparable endoprostheses which, in addition to replacing the acetabulum, also extend at least to the region of the os iliumare are known from the prior art. For example, a modular reinforcement system for the articular cavity of the hip joint is known from DE 697 29 265 T2. Individual planar add-on modules are provided which can be connected to an acetabulum replacement, and from which selected modules can also extend at least over the os illium. The add-on elements disclosed therein are releasably attached to the acetabulum where they do not serve to replace bone defects in the os illium, for example, but rather enhance the anchoring strength of the acetabulum replacement.

DE 197 47 357 C1, which describes a development of the pelvic partial endoprosthesis disclosed in DE 197 00 160 C1, also discloses a pelvic partial endoprosthesis, wherein a bridge guided over the os ilium and releasably attached to the acetabulum replacement—designated as a bridging piece therein—can be attached to also affix the overall prosthesis created in this manner to this pelvic part. This additional element serves to stabilize the partial endoprosthesis even when the pubic bone is severed, supports the clamping of the fracture by means of claws inserted into the opening between the os ilium, os ischium and os pubis, and exerts tension there, drawing the fracture together.

The latter two known solutions from the prior art especially do not serve to bridge or repair a more extensive bone defect, which also extends into the os ilium, resulting for example from serious injury, that can, however, arise in particular from pelvic bone tumors.

DESCRIPTION OF THE INVENTION

With the invention, an endoprosthesis for the partial replacement of the human pelvic bone of the initially-cited type will be presented by means of which bone replacement and stabilization in the region of both the acetabulum as well as defective sections of the os ilium can be achieved with a single prosthesis which, in other words, is suitable for restoring the stability and load-bearing capacity of this section of the skeleton with a single part, even when there are large bone defects in the pelvic region, and for retaining or restoring the articulation and mobility in this region.

This object is achieved according to the invention in that the second section, proceeding from the first section, extends flattened beyond the edge of the first partially-spherical recess and is connected integrally with the first section, and that furthermore a second, partially-spherical recess is introduced into the second section. This second, partially-spherical recess is introduced in the same direction as the recess serving as a replacement for the acetabulum, and is hence curved concave when viewing the endoprosthesis according to the invention from above from a direction running in the same direction of curvature (i.e., on the side visible from the surface after the endoprosthesis is inserted into the human pelvic bone), and it is convex when viewed from the opposite, back side.

This prosthesis is highly stable given the design according to the invention of an integral endoprosthesis, i.e., an integral connection between the first section with the first partially-spherical recess and the second section with the second partially-spherical recess, and the loads exerted on the prosthesis by the musculoskeletal system can be safely absorbed and reliably deflected toward the anchoring regions of the prosthesis and the remaining pelvic bone, and transferred from there to the natural skeleton.

The second spherical recess according to the invention provided in the second section lies at the cranial end of the endoprosthesis in the installed position, whereas the acetabulum-replacing, first partially-spherical recess lies at the caudal end of the endoprosthesis and serves to securely and reliably support the endoprosthesis in this section on the remaining residual bone of the os ilium. In addition, corresponding support surfaces formed to be complementary to the second, partially-spherical recess can be easily created in the remaining bone material of the os ilium.

The expression "partially-spherical" as used in the present description means that the surface shape of the corresponding recesses lie and correspondingly run, at least sectionally, on a spherical section, i.e., a partial sphere.

Advantageously, a wider and flattened edge protruding at an angle lies on the side opposite the first, partially-spherical recess of the second partially-spherical recess, and is integrally formed on it. With this edge, the precise shape of which ideally simulates the contour of the surface of the os ilium, the endoprosthesis can abut the bone section in the region surrounding the second partially-spherical recess, and accordingly enables an additional statically effective transmission of force up to, and introduction of force into, the os ilium.

Outwardly extending tabs integrally formed in the first and/or second section are advantageously provided, each of which has at least one passage for guiding fasteners, especially bone screws. One of these tabs may in principle be sufficient to anchor the endoprosthesis; however, at least two or more of these tabs is preferred. These tabs do not necessarily have to run straight in a plane; they can also have angles for introducing anchors from different angles into the remaining bone of the patient, especially in the form of bone screws, and secure the endoprosthesis according to the invention.

Additional passages for guiding a fastener can be provided in the first and/or second partially-spherical recess. Corresponding passages should be provided especially in the first partially-spherical recess to secure the endoprosthesis in the region of the acetabulum replacement subject to particular stress during subsequent use of the endoprosthesis.

With the endoprosthesis according to the invention, a penetration can be provided, arranged in particular at a transition region between the first and second section and between the first and second partially-spherical recess, which is otherwise surrounded by the material of the integrally formed endoprosthesis. Such a penetration offers a savings in material, thereby reducing the weight of the endoprosthesis. Furthermore, the penetration provides the surgeon with the opportunity of looking through the penetration onto the region lying underneath when aligning and inserting the endoprosthesis, and accordingly an improved orientation in the surgical field. The material sections which connect the first and second sections next to the penetration then also serve to bridge a defect in the bone of the patient that is to be bridged by means of the endoprosthesis.

In particular, the second partially-spherical recess in the endoprosthesis according to the invention is designed such that the partially-spherical region drawn out of the surface of the endoprosthesis in the direction into which the first partially-spherical recess also extends is formed around a region of the second section lying at a distance from the first partially-spherical recess, i.e., at a cranial end of the endoprosthesis. The penetration designed according to the aforementioned advantageous development then lies in particular between these regions of the first and second partially-spherical recess. On the one hand, this saves endoprosthesis material, and on the other hand, material can be obtained to form the second partially-spherical recess by punching this penetration out of the surface of the endoprosthesis.

With the endoprosthesis according to the invention, indentations can be provided in the region of the first partially-spherical recess on the concave side of the material. These help to fix the articular cavity inserted into prosthesis and improve the connection, particularly with adhesive or cement.

Likewise, indentations can be provided in the region of the second partially-spherical recess on the convex side of the material. These can help improve the anchoring of the endoprosthesis on the residual bone material in this region, for example when additionally fixing the endoprosthesis with bone cement.

A structure simulating the cranial roof of the articular cavity is advantageously provided in the region in which the second section abuts the first partially-spherical recess and its edge. The cranial roof of the articular cavity in the natural hip joint is necessary for avoiding hip luxations while moving. Since this part of the natural bone is sufficiently deteriorated or altered in bone defects to be treated with the endoprosthesis according to the invention for it to be dysfunctional, it must also be reconstructed or re-created for the formed artificial joint to function in the future. In this regard, it is useful to integrate this structure in the integral design of the endoprosthesis according to the invention and provide it in the prosthesis.

The endoprosthesis according to the invention is formed in particular from a metal that it is preferably highly polished and can with particular advantage consist of titanium or a titanium alloy. In endoprosthetics, such materials are tried and tested as particularly stable in transmitting the arising force and in terms of their biocompatibility.

The endoprosthesis according to the invention is in particular custom-made for the affected patients depending on the individual findings. Typically, using known imaging procedures (such as computerized tomography), images are taken of the worn pelvic section of the patient to be treated, a model is created on the basis of this image, for example using the rapid prototyping procedure, and the planning of an appropriate endoprosthesis is undertaken on the basis of this model. The production of such an endoprosthesis can in particular comprise a casting step in a casting mold, and further processing of the cast part for example by grinding and polishing. It is also possible, however, to first create a body mold and then produce a blank of the endoprosthesis by cold shaping such as cold stamping, or hot shaping such as forging, which is then finished by subsequent processing such as grinding and polishing.

BRIEF DESCRIPTION OF THE DRAWINGS

Additional advantages and features of the invention are offered in the subsequent description of an exemplary embodiment with reference to the accompanying figures. In the following.

WAYS TO IMPLEMENT THE INVENTION

The figures show various exemplary embodiments of endoprostheses according to the invention for a partial replacement of the human pelvic bone from different views. The figures also show the implantation position of such endoprostheses, as well as an illustration for planning an endoprosthesis according to the invention with reference to a model of a defective pelvic bone of a patient. The features are not at all restrictive; together with the following description, they are merely geared at explanation and a better understanding of the invention.

Figure 1:
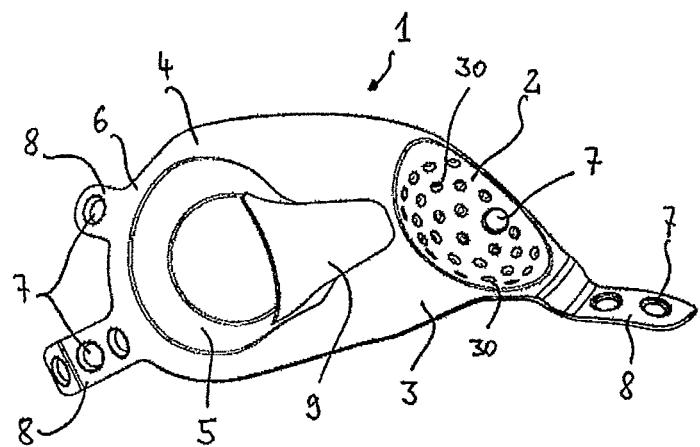
FIG. 1 shows a first exemplary embodiment of an endoprosthesis according to the invention for the partial replacement of the human pelvic bone in a plan view, i.e., from the side facing away from the bone in implantation position.
Figure 2:
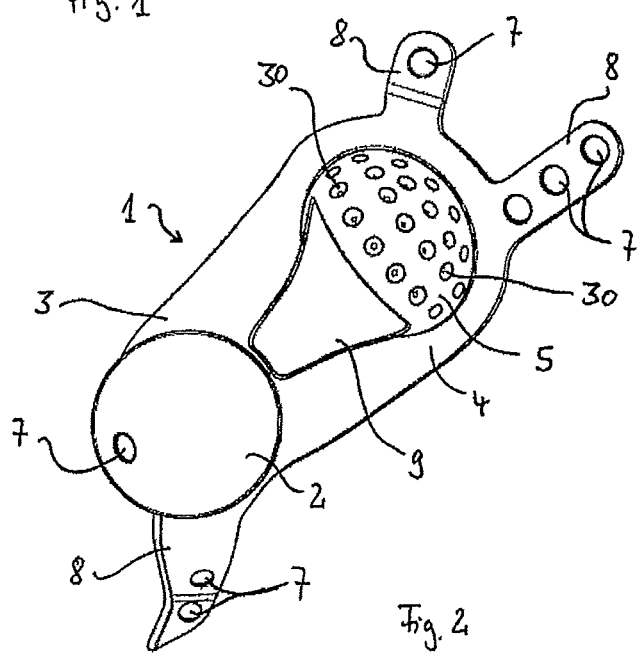
FIG. 2 shows the endoprosthesis from FIG. 1 in a view from below.

FIGS. 1 and 2 to show a first exemplary embodiment of an endoprosthesis for the partial replacement of the human pelvic bone from different perspectives: one perspective from above, i.e., the exposed surface of the endoprosthesis (FIG. 1) facing away from the bone in implantation position, and one perspective from below, i.e., the surface lying against the bone in implantation position (FIG. 2). This endoprosthesis is designated with reference number 1 in the first exemplary embodiment. It has a first partially-spherical recess 2 in a first section 3, which first partially-spherical recess 2 serves as a replacement of the acetabulum in the pelvic bone of the human patient to be treated.

A second partially-spherical recess 5 is provided in a second section 4 which lies against the os ilium of the patient when the endoprosthesis 1 is in the implanted state. A flattened edge 6 is formed around this second, partially-spherical recess 5 and largely surrounds it. Proceeding from this edge 6 and neighboring the first partially-spherical recess 2, mounting tabs 8 provided with mounting holes 7 are formed on the endoprosthesis 1 by means of which the endoprosthesis can be secured to the surrounding bone material of the pelvis by guiding bone screws through the mounting hole 7 and fixing them in the pelvic bone. An additional mounting hole 7 can be seen in the first partially-spherical recess 2 which simulates the acetabulum. This mounting opening 7 in the partially-spherical recess 2 also serves for fixation, especially the primary fixation of the endoprosthesis 1, in this case in the particularly stressed region of the acetabulum which accommodates the artificial articular cavity.

It can also be seen that the mounting tabs 8 are not run and flat but rather angled and offset. The contour of the mounting tabs 8 is selected and modeled according to the anatomical conditions of the surface of the pelvic bone of the patient to be provided with the endoprosthesis.

The endoprosthesis 1 is integrally formed, in particular with an integral connection between the two sections 3 and 4.

Adjacent to a region integrally connecting these sections, a penetration 9 is however also provided, which in this case forms an opening extending through the surface of the endoprosthesis 1. The penetration reduces the material and weight of the endoprosthesis 1 and allows the surgeon to look through the penetration while aligning and setting the endoprosthesis 1 at the regions underneath which results in an improvement of the surgeon's orientation in the surgical field.

Indentations 30 arranged in a regular pattern are created in the concave surface of the partially-spherical recess 2 lying on the top side of the endoprosthesis 1, and on the convex outer surface of the second partially-spherical recess 5 lying on the bottom side of the prosthesis. These are readily discernible in FIGS. 1 and 2. These indentations 30 serve to enlarge the respective surface for an improved connection of the regions having their surfaces enlarged in this manner with an artificial articular cavity inserted into the concave seat of the first partially-spherical recess 2 to fix the articular cavity with an adhesive or cement, or to mount the second partially-spherical recess 5 on the pelvic bone of the patient in the region of the os ilium.

Figure 3:
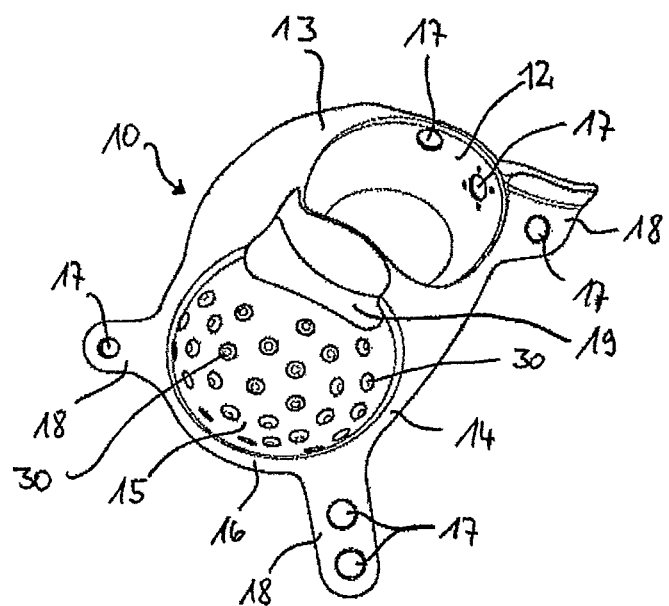
FIG. 3 shows a view from below of a second exemplary embodiment of an endoprosthesis according to the invention.

FIG. 3 shows a second exemplary embodiment of an endoprosthesis 10 according to the invention, in this instance from the bottom side. This endoprosthesis 10 also shows a first partially-spherical recess 12 which serves as a replacement for the acetabulum and is arranged in a first section 13. It can also be seen that a second partially-spherical recess 15 is arranged in the second section 14 of the endoprosthesis 10. This second section 14 of the portrayed endoprosthesis 10 is also provided to be placed on the pelvic bone of the patient in the region of the os ilium; the partially-spherical recess 15 is inserted in a correspondingly created recess in the os ilium and is connected to this section of the pelvis.

In this case as well, a flattened edge 16 can be seen that surrounds a large area around the second partially-spherical recess 15, and the edge extends in any case beyond the section that is opposite the first partially-spherical recess 12. As is the case with the peripheral edge 6 in the previously depicted example, this peripheral edge 16 serves as a smooth support against the pelvic bone material of the as ilium of the patient.

Mounting tabs 18 penetrated by mounting holes 17 are also arranged on this endoprosthesis 10, and additional mounting holes 17 can be seen in the first partially spherical recess 12. Here as well, the mounting tabs 18 and mounting hole 17 serve to anchor the endoprosthesis 10 to the pelvic bone of the patient. At least primary stability of the endoprosthesis 10 is obtained by inserting bone screws through the mounting holes 17 and fixing the bone screws in the pelvic bone.

Indentations 30 can also be discerned in this case in the convex exterior of the second partially spherical recess 15. Such indentations 30 are also provided in the concave interior of the partially spherical recess 12 which cannot be seen in this figure. Finally, the endoprosthesis 10 also has a penetration 19 in the otherwise integrally formed surface, and in the region between the first section 13 and second section 14.

Figure 4:
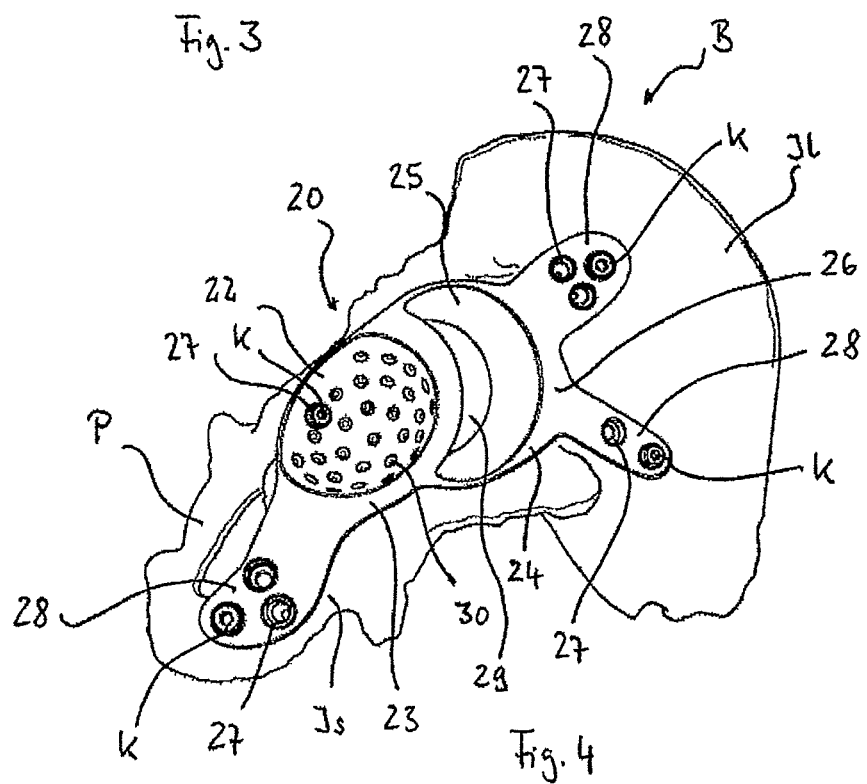
FIG. 4 shows a third exemplary embodiment of an endoprosthesis according to the invention in an implantation position in the pelvis.
Figure 5:
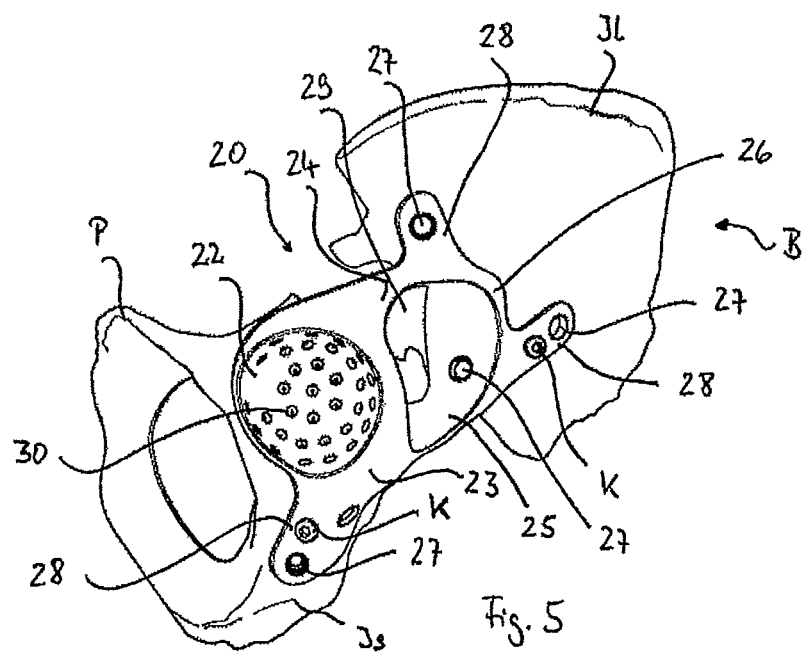
FIG. 5 shows the exemplary embodiment from FIG. 4 in the implantation position in the pelvis shown from another perspective.

FIGS. 4 and 5 show a third exemplary embodiment of an endoprosthesis 20 according to the invention in an implantation position in a human pelvic bone B.

The endoprosthesis 20 which is also shown here in its implantation position in the pelvic bone B has a first, partially-spherical recess 22 that is arranged in a first section 23 of the endoprosthesis 20. This first partially spherical recess 22 in the endoprosthesis 20 simulates the acetabulum of the patient which lies in the connecting region between the os ilium II, os pubis P and os ischium Is. A second partially spherical recess 25 is arranged in a second section 24 of the endoprosthesis 20, which second section 24 extends over the os ilium II. In the implantation position shown here, this is inserted in a defect in the os ilium II in the patient, and a mating shape of the partially spherical recess 25 was correspondingly produced in the region of this defect in the previous bone. Around the partially spherical recess 25, in particular on the edge region of the second partially spherical recess 25 opposite the first partially spherical recess 22, a smooth and peripheral edge 26 is formed which lies against the surface of the os ilium II, and forces accumulating there, which act on the endoprosthesis 20, are transferred into the healthy and stable region of the os ilium II there.

Mounting tabs 28 provided with mounting holes 27 are also arranged on this endoprosthesis 20. It can be seen in this case how the mounting tabs 28 neighboring the second, partially spherical recess 25 are placed on the os ilium II, whereas the mounting tabs 28 neighboring the first partially spherical recess 22 run along the os ischium Is. A mounting hole 27 in the first partially spherical recess 22 can also be seen in FIG. 4, and a mounting hole 27 in the second partially spherical recess 25 can be seen in FIG. 5. Heads of bone screws K, drawn for purposes of representation, with which the endoprosthesis 20 is secured to the pelvic bone B, can be seen in some of the mounting holes 27.

At a transitional region between the first section 23 and second section 24, a penetration 29 can also be seen in this endoprosthesis 20.

As is the case with the previously presented and described endoprostheses 1 and 10, the convex interior of the first partially spherical recess 22 can be seen here as well with easily discernible indentations 30. Such indentations 30 are also provided on the concave exterior of the second partially spherical recess 25 (not shown in this case) in the region where the recess touches the os ilium II.

As is the case with the above-described and presented endoprostheses 1 and 10, the endoprosthesis 20 is integrally formed. In the portrayed exemplary embodiment as in the case of the above-described exemplary embodiments, it consists of a metal, especially a titanium or titanium alloy, and is advantageously highly polished.

Figure 6:
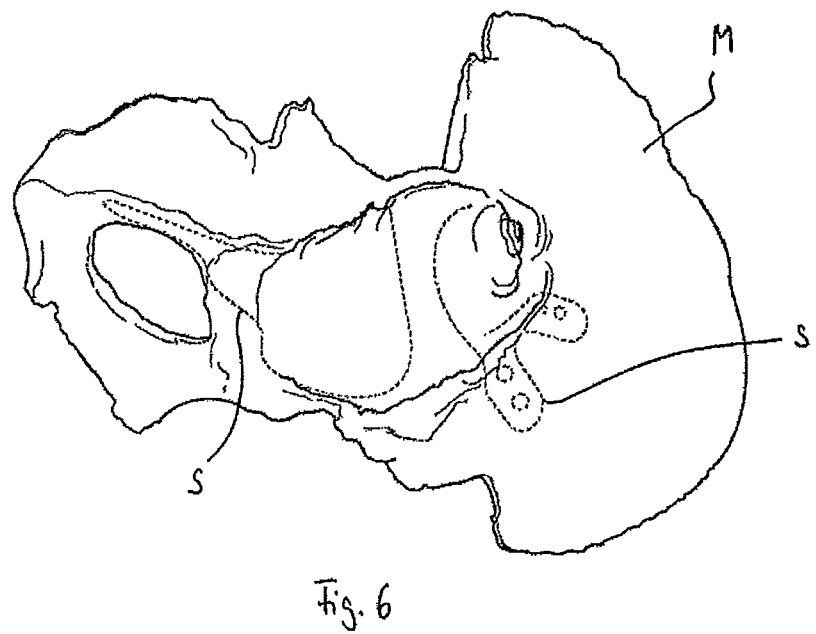
FIG. 6 shows an illustration of a plan of a prosthesis with reference to a model simulating the defective pelvic bone of the patient.

The endoprosthesis according to the invention is typically not manufactured as a finished, mass-produced item, but is rather individually planned and produced for a patient with extensive symptoms of deterioration or bone defects such as tumor defects in the pelvic region, which defects extend beyond the acetabulum into the os ilium. Planning is carried out using a model M of a pelvic bone of the patient that for example was created by means of rapid prototyping according to findings from imaging procedures such as computerized tomography (CT). During such planning, a medical technician responsible for planning first sketches a suitable position and orientation of the endoprosthesis to be fabricated on the model M in a way indicated in FIG. 6 by the dashed sketch lines S.

Proceeding from the model M, the specified data and geometric dimensions for the implant to be created are digitized, and a fitting and individually tailored endoprosthesis can be created with reference to these specifications. This production can for example be in the form of a cast part, wherein a casting mold individually specified for the patient is created, and a blank of the endoprosthesis is cast therein. This blank is then finished by further processing, especially introducing the mounting holes and indentations as well as a final surface processing, especially a high-gloss polish. Alternatively, procedures are possible in which a forging die or die mold is individually set up suitable for the patient, and the endoprosthesis is shaped into a partially finished product by hot or cold working a substantially flat blank and then correspondingly finished by introducing the mounting holes and forming the indentations followed by surface processing.

LIST OF REFERENCE NUMBERS

1 Endoprosthesis
2 Partially spherical recess
3 Section
4 Section
5 Partially spherical recess
6 Edge
7 Mounting hole
8 Mounting tab
9 Penetration
10 Endoprosthesis
12 Partially spherical recess
13 Section
14 Section
15 Partially spherical recess
16 Edge
17 Mounting hole
18 Mounting tab
19 Penetration
20 Endoprosthesis
22 Partially spherical recess
23 Section
24 Section
25 Partially spherical recess
26 Edge
27 Mounting hole
28 Mounting tab
29 Penetration
30 Indentation
B Pelvic bone
II Os Ilium
Is Os ischium
K Bone screw
P Os pubis
S Sketch line

The invention claimed is:

1. An endoprosthesis for the partial replacement of the human pelvic bone (B) in the region of the acetabulum as well as the os ilium (II) wherein the endoprosthesis has an interior surface and an exterior surface and the interior surface is adapted to be placed in contact with the pelvic bone (B); wherein the endoprosthesis includes a first section which has a first partially spherical recess that serves as a replacement for the acetabulum as well as a second section for resting against the os ilium (II), wherein the second section, proceeding from the first section, extends flattened beyond an edge of the first partially spherical recess and is integrally connected to the first section, and a second partially spherical recess is introduced in the second section; and when the exterior surface of the endoprosthesis is viewed, the first partially spherical recess is concave in shape and the second partially spherical recess is concave in shape.

2. The endoprosthesis according to claim 1, further comprising at least one wider and flattened edge protruding at an angle and formed on the second partially-spherical recess on a side opposite the first, partially-spherical recess.

3. The endoprosthesis according to claim 1, wherein outwardly extending tabs integrally formed in the first or second section are provided which each have at least one passage for guiding fasteners.

4. The endoprosthesis according to claim 3, further comprising a penetration arranged between the first and second section and between the first and second partially-spherical recess, and which is otherwise surrounded by material of the integrally formed first and second sections.

5. The endoprosthesis according claim 4, wherein indentations are arranged in a region of the first partially spherical recess on a concave side of the material.

6. The endoprosthesis according to claim 4, wherein indentations are arranged in a region of the second partially spherical recess on the convex side of the material.

7. The endoprosthesis according to claim 1, wherein at least one passage is arranged for guiding a fastener in the first partially spherical recess.

8. The endoprosthesis according to claim 1, wherein a structure simulating the cranial roof of the articular cavity of a particular patient being treated is provided in a region in which the second section abuts the edge of first partially-spherical recess.

9. The endoprosthesis according to claim 1 comprising a preferably highly-polished metal.

10. The endoprosthesis according to claim 9, wherein the highly-polished metal is titanium or a titanium alloy.

11. The endoprosthesis according to claim 1 produced by casting and further processing a cast part produced thereby.

12. The endoprosthesis according to claim 1 produced by cold or hot working from a substantially flat starting workpiece and further processing of a shaped part created in this manner.

13. The endoprosthesis according to claim 1, wherein the second section, proceeding from the first section and the second partially spherical recess serves as a replacement for additional areas of the pelvic bone.

14. The endoprosthesis according to claim 1, wherein the first partially spherical recess and the second partially spherical recess are separated a distance from each other by a region that is of a width from a first side edge to a second side edge that is similar to a width of the first section and the second section.

* * * * *